[19] United States Patent
Nishikido et al.

[11] Patent Number: 4,477,659
[45] Date of Patent: Oct. 16, 1984

[54] CEPHALOSPORIN COMPOUND

[75] Inventors: Joji Nishikido; Eiji Kodama, both of Fuji; Mitsuru Shibukawa, Yokohama, all of Japan

[73] Assignee: Asahi Kasei Kogyo Kabushiki Kaisha, Tokyo, Japan

[21] Appl. No.: 388,937

[22] Filed: Jun. 16, 1982

[30] Foreign Application Priority Data

Jun. 24, 1981 [JP]  Japan ................................. 56-96503

[51] Int. Cl.³ ................. C07D 501/57; A61K 31/545
[52] U.S. Cl. ...................................... 544/21; 544/20; 544/26; 544/27; 544/28; 424/246
[58] Field of Search ...................... 544/25, 27, 22, 21, 544/28, 29; 424/246

[56] References Cited

U.S. PATENT DOCUMENTS 3,499,893  3/1970  Crast ....................................... 544/22
3,627,760  12/1971  Bickel et al. ............................ 544/22
4,229,573  10/1980  Shibuya et al. ........................ 544/21

Primary Examiner—Nicholas S. Rizzo
Attorney, Agent, or Firm—Finnegan, Henderson, Farabow, Garrett & Dunner

[57] ABSTRACT

A cephalosporin compound of the general formula (I):

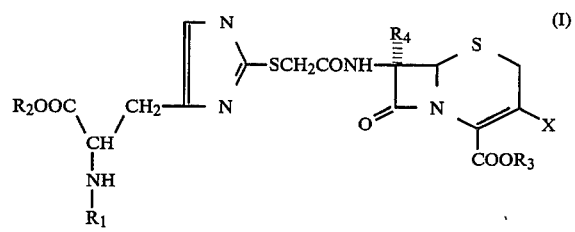

wherein

X is a hydrogen atom, a chlorine atom, a methyl group, a methoxy group, an acetoxymethyl group or —CH$_2$SHet wherein Het is a 5- or 6-membered heterocyclic ring containing therein 1 to 4 nitrogen, oxygen or sulfur atoms;

$R_1$, $R_2$ and $R_3$ each independently is a hydrogen atom or a protective group which can be pharmaceutically hydrolyzed; and $R_4$ is a hydrogen atom or a methoxy group;

and the pharmaceutically acceptable salts thereof.

5 Claims, No Drawings

CEPHALOSPORIN COMPOUND

BACKGROUND OF THE INVENTION

1. Field of the Invention

This invention relates to novel cephalosporin compounds and the pharmaceutically acceptable salts thereof.

2. Description of the Prior Art

Most antibiotic compounds of penicillin and cephalosporin which have been actually used as a drug for remedy or prevention of infectious disease have a superior antibacterial activity but have little oral activity. Therefore, in the medical treatment by administering these drugs to patients, a trained medical expert has been required. Accordingly, development of cephalosporin antibiotic which can be orally administered and has strong antibacterial activities has been greatly desired, and many studies have been done for a long period of time. Of cephalosporin antibiotic compounds, only compounds having a specific structure such as cephalexin and its analogue have been actually used.

Most studies meeting the above described purpose relate to render the 4-position carboxylic acid group of cephalosporin compounds lipo-soluble to give the lipo-soluble cephalosporin derivatives such as the acetoxymethyl ester derivatives, the pivaloyloxymethyl ester derivatives and the methoxymethyl ester derivatives. However, these cephalosporin derivatives have not been put to practical use because of their low intestinal absorbability.

The inventors of this invention found that the intestinal absorption of the cephalosporin derivatives could be accelerated by bonding an oligopeptide with the cephalosporin derivatives. Thereafter, the inventors continued the study to provide novel cephalosporin compounds having the intestinal absorbability.

SUMMARY OF THE INVENTION

An object of this invention is to provide novel cephalosporin compounds.

Another object of this invention is to provide a novel antibacterial agent.

Accordingly, the present invention in one embodiment provides cephalosporin compounds having the general formula (I),

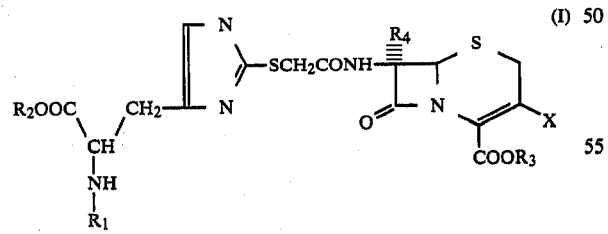

wherein
X is a hydrogen atom, a chlorine atom, a methyl group, a methoxy group, an acetoxymethyl group or —CH₂SHet wherein Het is a 5- or 6-membered heterocyclic ring containing therein 1 to 4 nitrogen, oxygen or sulfur atoms;
$R_1$, $R_2$ and $R_3$ each independently is a hydrogen atom or a protective group which can be pharmaceutically hydrolyzed; and
$R_4$ is a hydrogen atom or a methoxy group; and the pharmaceutically acceptable salts thereof.

DESCRIPTION OF PREFERRED EMBODIMENTS

Exemplary X of the formula (I) includes a hydrogen atom, a chlorine atom, a methyl group, a methoxy group, an acetoxymethyl group and —CH₂SHet wherein Het is a 5- or 6-membered heterocyclic ring containing therein 1 to 4 nitrogen, oxygen or sulfur atoms such as

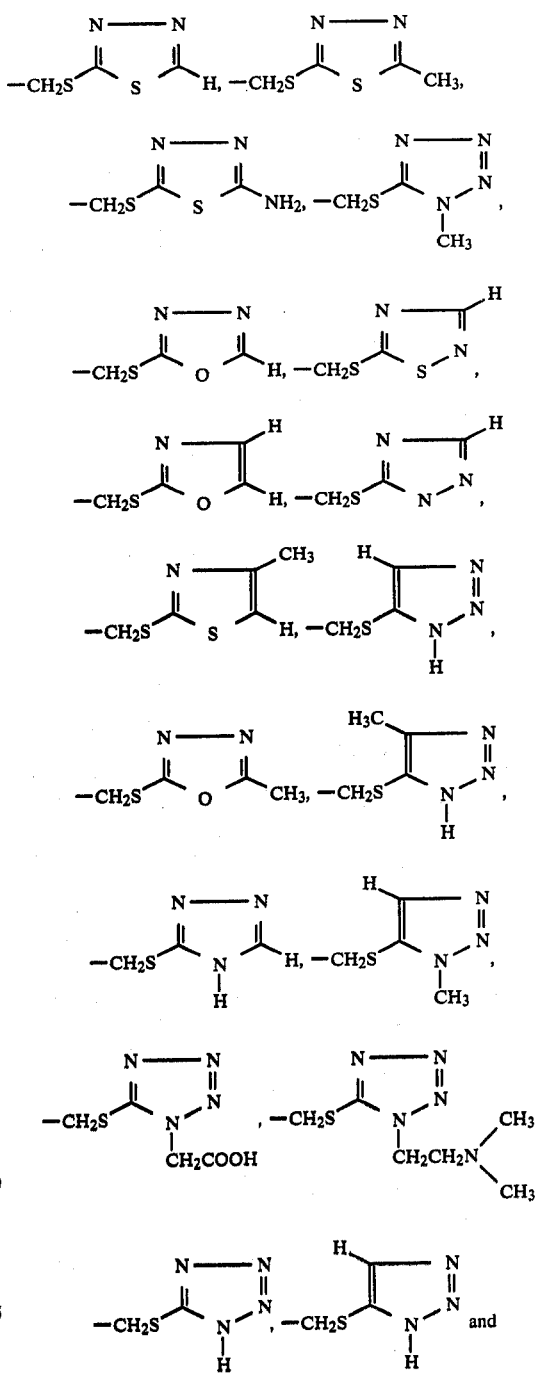

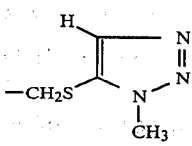

Preferred X of the formula (I) includes a hydrogen atom, a chlorine atom, a methyl group, a methoxy group, an acetoxymethyl group,

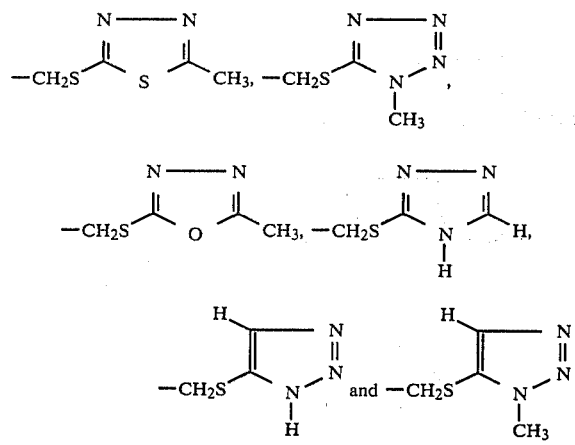

Exemplary $R_1$ of the formula (I) includes a hydrogen atom, a formyl group and a $C_{1-3}$ alkyl group such as methyl, ethyl, n-propyl and i-propyl group. Preferred $R_1$ includes a hydrogen atom, a formyl group and a methyl group.

Exemplary $R_2$ and $R_3$ of the formula (I) include a hydrogen atom, a methoxymethyl group, an acetoxymethyl group, a tert-butylcarboxymethyl group, an 1'-ethoxycarbonyloxyethyl group and a phthalidyl group. Referred $R_2$ and $R_3$ include a hydrogen atom, an acetoxymethyl group and a tert-butylcarboxymethyl group.

The cephalosporin compounds of the formula (I) may be in the form of inner salts. Further, the cephalosporin compounds of the formula (I) can be converted into the pharmaceutically acceptable salts of an alkali metal such as sodium; the salts of a basic organic compound such as L-lysine; the salts of an inorganic acid such as hydrochloric acid; and the salts of an organic acid such as formic acid and acetic acid.

The cephalosporin compounds of the formula (I) can have an optical isomer in the histidine part of the cephalosporin compound. All of the D-, L- and DL-isomers can be employed in this invention.

Exemplary cephalosporin compounds of this invention includes:
(1) 7-$\beta$-[4-(2'-amino-2'-carboxy)ethylimidazol-2-yl-thioacetamido]-3-acetoxymethyl-3-cephem-4-carboxylic acid;
(2) 7-$\beta$-[4-(2'-amino-2'-carboxy)ethylimidazol-2-yl-thioacetamido]-3-[(1-methyl-1H-tetrazol-5-yl)thiomethyl]-3-cephem-4-carboxylic acid;
(3) 7-$\beta$-[4-(2'-amino-2'-carboxy)ethylimidazol-2-yl-thioacetamido]-3-[(1-methyl-1H-tetrazol-5-yl)thiomethyl]-3-cephem-4-carboxylic acid hydrochloric acid salt;
(4) 7-$\beta$-[4-(2'-amino-2'-carboxy)ethylimidazol-2-yl-thioacetamido]-3-[2-(2-methyl-1,3,4-thiazolyl)thiomethyl]-3-cephem-4-carboxylic acid;
(5) 7-$\beta$-[4-(2'-amino-2'-carboxy)ethylimidazol-2-yl-thioacetamido]-3-[(1,3,4-triazole)thiomethyl]-3-cephem-4-carboxylic acid;
(6) 7-$\beta$-[4-(2'-amino-2'-carboxy)ethylimidazol-2-yl-thioacetamido]-3-[(1,3,4-triazole)thiomethyl]-3-cephem-4-carboxylic acid formic acid salt;
(7) 7-$\beta$-[4-(2'-amino-2'-carboxy)ethylimidazol-2-yl-thioacetamido]-3-[(1,2,3-triazole)thiomethyl]-3-cephem-4-carboxylic acid;
(8) 7-$\beta$-[4-(2'-amino-2'-carboxy)ethylimidazol-2-yl-thioacetamido]-3-[(2-methyl-1,3,4-oxadiazole)thiomethyl]-3-cephem-4-carboxylic acid;
(9) 7-$\beta$-[4-(2'-amino-2'-carboxy)ethylimidazol-2-yl-thioacetamido]-3-[(1-methyl-1H-1,2,3-triazole)thiomethyl]-3-cephem-4-carboxylic acid;
(10) 7-$\beta$-[4-(2'-amino-2'-carboxy)ethylimidazol-2-yl-thioacetamido]-3-methyl-3-cephem-4-carboxylic acid;
(11) 7-$\beta$-[4-(2'-amino-2'-carboxy)ethylimidazol-2-yl-thioacetamido]-3-methoxy-3-cephem-4-carboxylic acid;
(12) 7-$\beta$-[4-(2'-amino-2'-carboxy)ethylimidazol-2-yl-thioacetamido]-3-chloro-3-cephem-4-carboxylic acid;
(13) 7-$\beta$-[4-(2'-amino-2'-carboxy)ethylimidazol-2-yl-thioacetamido]-3-cephem-4-carboxylic acid;
(14) 7-$\beta$-[4-(2'-amino-2'-carboxy)ethylimidazol-2-yl-thioacetamido]-7$\alpha$-methoxy-3-acetoxymethyl-3-cephem-4-carboxylic acid;
(15) 7-$\beta$-[4-(2'-amino-2'-carboxy)ethylimidazol-2-yl-thioacetamido]-7$\alpha$-methoxy-3-[(1-methyl-1H-tetrazol-5-yl)thiomethyl]-3-cephem-4-carboxylic acid;
(16) 7-$\beta$-[4-(2'-amino-2'-carboxy)ethylimidazol-2-yl-thioacetamido]-7$\alpha$-methoxy-3-[(1-methyl-1H-tetrazol-5-yl)thiomethyl]-3-cephem-4-carboxylic acid diacetoxymethyl ester;
(17) 7-$\beta$-[4-(2'-formamido-2'-carboxy)ethylimidazol-2-yl-thioacetamido]-3-[1-methyl-1H-tetrazol-5-yl)thiomethyl]-3-cephem-4-carboxylic acid;
(18) 7-$\beta$-[4-(2'-methylamido-2'-carboxy)ethylimidazol-2-yl-thioacetamido]-3-[2-(2-methyl-1,3,4-thiazolyl)-thiomethyl]-3-cephem-4-carboxylic acid; and
(19) 7-$\beta$-[4-(2'-amino-2'-carboxy)ethylimidazol-2-yl-thioacetamido]-7$\alpha$-methoxy-3-[(1-methyl-1H-tetrazol-5-yl) thiomethyl]-3-cephem-4-carboxylic acid ditert-butylcarboxymethyl ester.

The cephalosporin compounds of the general formula (I) of this invention can be prepared by the following method.

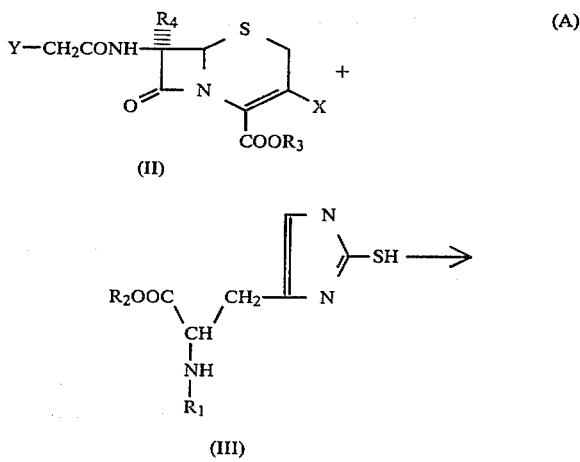

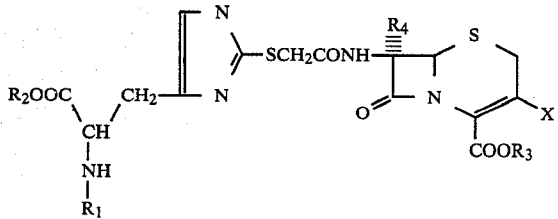

(I)

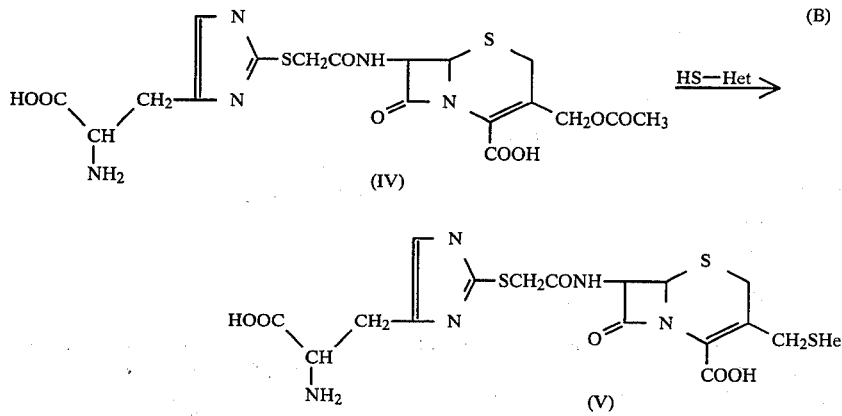

wherein X, $R_1$, $R_2$, $R_3$ and $R_4$ are the same as defined in the formula (I) and Y is a halogen atom.

Exemplary Y in the compound (II) includes a chlorine atom, a bromine atom and an iodine atom, and a bromine atom is preferred.

The reaction (A) between the compound of the formula (II) and the compound of the formula (III) can be carried out in the presence of an organic base or an inorganic base and a reaction medium. Exemplary organic bases include pyridine and trialkylamines such as triethylamine. Exemplary inorganic bases include alkali metal carbonates and alkali metal bicarbonates such as sodium bicarbonate. The reaction media which can be employed in the reaction (A) include water, organic solvents which are inert to the compounds (II) and (III)

and mixtures thereof. Preferred reaction media include water, acetone and alcohols such as methanol.

The reaction (A) can be carried out at a temperature of $-20°$ C. to $35°$ C. for 30 minutes to 40 hours.

Some cephalosporin compounds of this invention can be prepared by the following method.

wherein Het is the same as defined in the formula (I).

The reaction (B) can be carried out in a reaction medium by adjusting the pH of the reaction solution to 6 to 7. Exemplary reaction media which can be employed include water and a water-containing organic solvent. Preferred organic solvents include acetone, methanol and ethanol.

The reaction (B) can be carried out at a temperature of 15° C. to 80° C. The reaction period of time which can be employed in the reaction (B) varies depending upon the type of the reactant HS-Het and the reaction temperature, and generally ranges from one hour to 10 hours.

The compound of the formula (V) obtained in the reaction (B) can be purified by subjecting the compound (V) to column chromatography packed with Amberlite XAD-II (product of Rohm and Haas Company). This purification can be easily carried out with high yield by protecting the amino group of the histidine part in the compound (IV) with tert-butyloxycarbonyl group, and reacting the tert-butyloxycarbonylated compound thus obtained with HS-Het before the purification in accordance with the following equation:

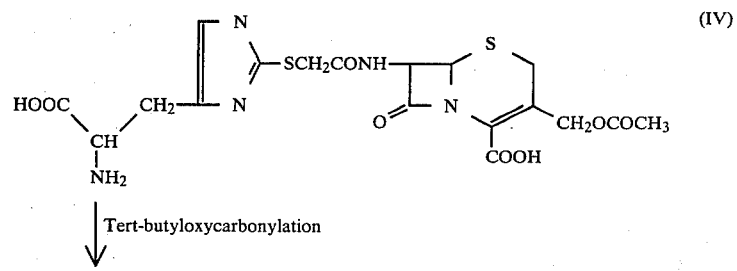

-continued

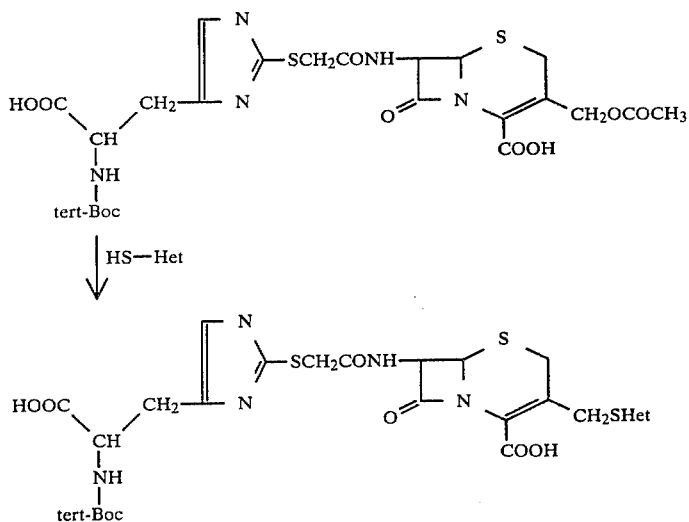

wherein Het is the same as defined in the formula (I).

After the purification, the tert-butyloxycarbonyl group can be eliminated with formic acid to obtain the compound of the formula (V).

Another method for preparing the compounds of the formula (V) is represented by the following equation.

The reaction between 7-amino-cephalosporanic acid (VI) and HS-Het can be carried out under the same reaction conditions as in the reaction (B).

The reaction between the compound of the formula (VII) and 2-thiolhistidine can be carried out under the same reaction conditions as in the reaction (A).

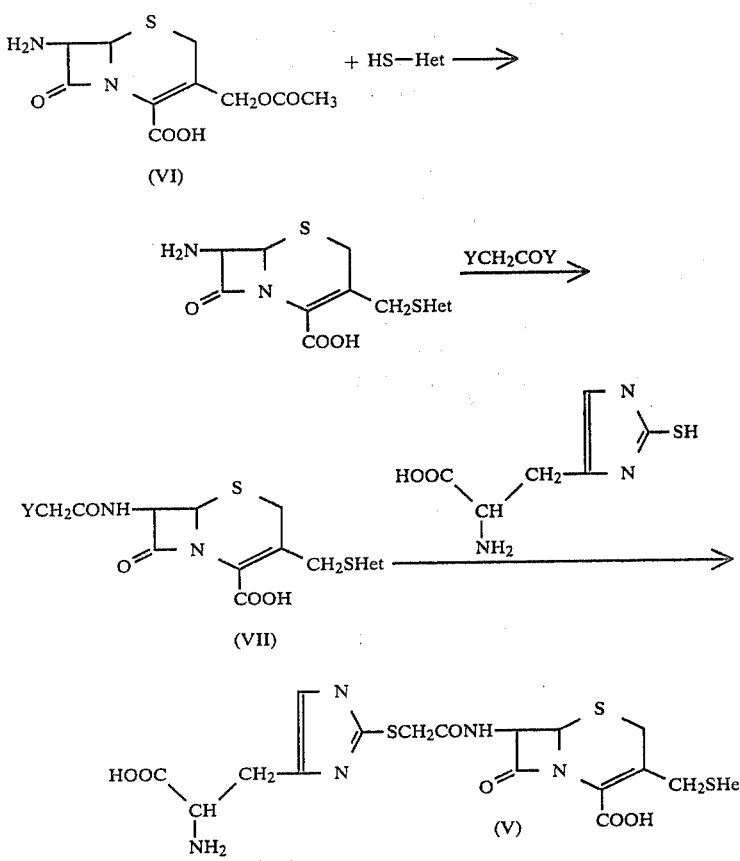

wherein Het and Y are the same as defined in the formulae (I) and (II), respectively.

The cephalosporin diester which can be represented by the formula (I) of this invention can be prepared by the same method as the following.

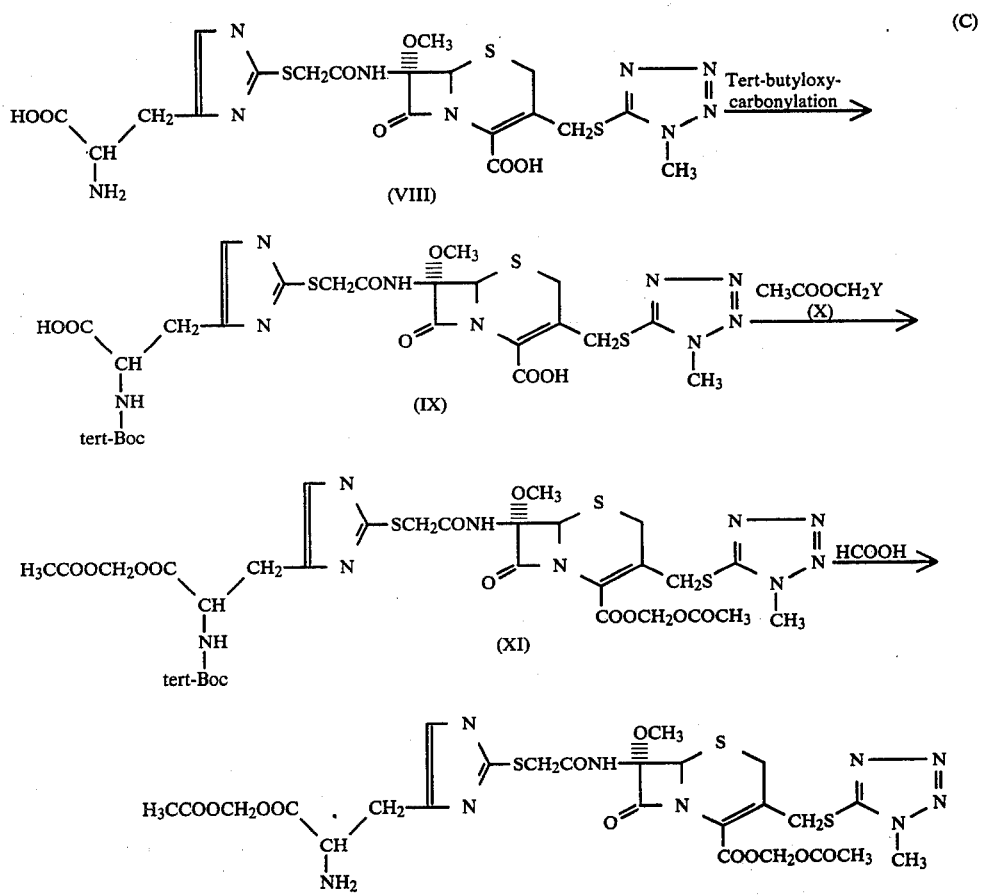

wherein Y is the same as defined in the formula (II).

The reaction (C) between the compound of the formula (IX) and the compound of the formula (X) must be carried out after the compound of the formula (VIII) is tert-butyloxycarbonylated. The reaction (C) can be carried out in the presence of an organic base and an organic solvent which is inert to the compounds (IX) and (X). Exemplary organic bases include triethylamine and dicyclohexylamine. Exemplary organic solvents which can be employed in the reaction (C) include N,N-dimethylformamide, dimethyl sulfoxide, tetrahydrofuran, dioxane and methylene chloride.

The reaction (C) can be carried out at a temperature of $-10°$ C. to 40° C., preferably 0° C. to 30° C., for one to 40 hours.

The desired cephalosporin diester can be obtained by reacting the compound of the formula (XI) with formic acid under cooling with ice.

The cephalosporin compound of this invention whose amino group in the histidine part is formamide group can be prepared by treating the compound of the formula (V) in a mixture of acetic anhydride and formic acid at a temperature of 0° C. to 40° C.

The cephalosporin compounds (I) of this invention have a superior antibacterial activity to various kinds of pathogenic bacteria as shown in Table 4, and are useful as antibacterial agents.

TABLE 4

MIC Value ($10^8$ cells/ml)

| Bacterium | Cephalexin[1] | X: $-CH_2-\text{(N-methyl-tetrazolyl-S)}$ | X: $-CH_2-\text{(N-methyl-tetrazolyl-S)}$ *[2] | X: $-CH_2-\text{(methyl-thiadiazolyl-S)}$ | X: $-CH_2OCOCH_3$ |
|---|---|---|---|---|---|
| *Staph. aureus* | 3.1 | 1.6 | 1.6 | 1.6 | 3.1 |

TABLE 4-continued

MIC Value ($10^8$ cells/ml)

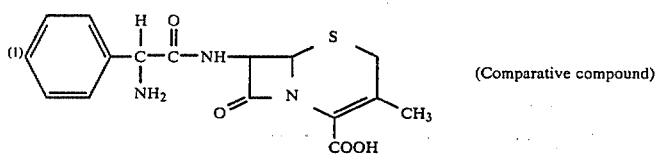

| Bacterium | Cephalexin[1] | X: <br>-CH₂-(N=N, N-CH₃) | X: <br>-CH₂-(N=N, N-CH₃)*[2] | X: <br>-CH₂-(N=N, S)-CH₃ | X: <br>-CH₂OCOCH₃ |
|---|---|---|---|---|---|
| ATCC 6538p *Staph. aureus* MS 27 | 50 | 12.5 | 12.5 | 25 | 12.5 |
| *Staph. aureus* 0003 | 50 | 12.5 | 12.5 | 25 | 12.5 |
| *E. Coli* NIHJ-JC2 | >100 | 25 | 12.5 | 50 | 50 |
| *E. Coli* W3630 | >100 | 25 | 12.5 | 50 | 100 |
| *E. Coli* W3630 ps 3 | >100 | 25 | 12.5 | 50 | 100 |
| *Klebs. pneumoniae* ATCC 10031 | 25 | 12.5 | 6.3 | 25 | 25 |
| *Salm enteritidis* Gaertner | >100 | 12.5 | 6.3 | 50 | 100 |

(1) [structure of cephalexin] (Comparative compound)

[2]The sign * represents that the histidine part of the compound shows the D-isomer. The compounds without the indication shows the L-isomers.

The cephalosporin compounds of this invention have not only the antibacterial activities to various kinds of bacteria but also the intestinal absorbability when the compounds are orally administered. It is surprising that the compounds of this invention have the intestinal absorbability though the 7-position of the compounds is a histidine derivative which is very different from a D-phenylglycine derivative of the cephalexin. Further, the cephalosporin compounds of this invention are excellent in durability of blood concentration of the cephalosporin compounds.

The cephalosporin compounds (I) of this invention can be orally administered singly or with a pharmaceutically acceptable carrier or dilution agent. Exemplary carriers and dilution agents include lactose, saccharose, starch, cellulose, calcium sulfate and gelatin. The novel compounds can be administered in the form of a tablet, a capsule, a suspension or a solution.

The following examples illustrate the present invention in more detail, but they are given for illustrative purposes only and are not to be construed as limiting the invention.

EXAMPLE 1

7-β-[4-(2'-amino-2'-carboxy)ethylimidazol-2-yl-thioacetamido]-3-acetoxymethyl-3-cephem-4-carboxylic acid was prepared in accordance with the following equation:

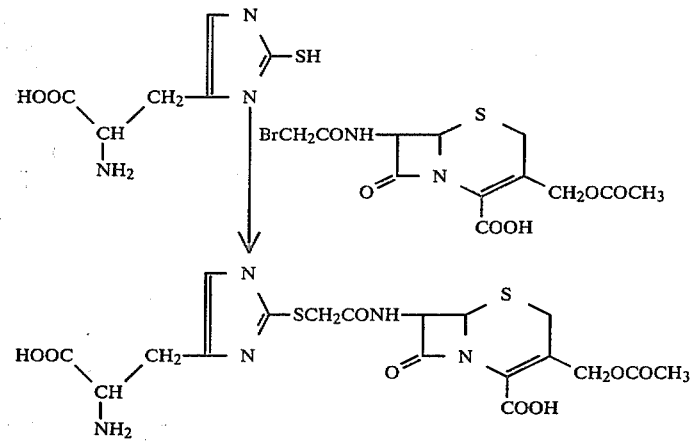

5.6 g of 2-thiol-L-histidine and 10 g of sodium bicarbonate were added to 400 ml of water, and dissolved at 30° C. with heating. After cooling the solution with ice, to the solution was added 12 g of 7-β-bromoacetamido- 3-acetoxymethyl-3-cephem-4-carboxylic acid and the reaction was carried out under cooling with ice for 2 hours. The pH of the product thus obtained was adjusted to 5–6 with 1N hydrochloric acid, and the product was subjected to column chromatography packed with Amberlite XAD-II (product of Rohm and Haas Company) by using water-methanol for the purification to give 10 g of a compound.

The compound was identified as 7-β-[4-(2′-amino-2′-carboxy)ethylimidazol-2-yl-thioacetamido]-3-acetoxymethyl-3-cephem-4-carboxylic acid by the following NMR spectrum of the compound.

| NMR Spectrum (in DMSO-d$_6$): | | |
|---|---|---|
| 9.40 ppm | —CH$_2$CONH— | doublet |
| 6.90 ppm | H-N=/-S— (imidazole) | singlet |
| 5.55 ppm | cephem H | multiplet |
| 5.06 ppm | cephem H | doublet |
| 4.87 ppm | —CH$_2$OCOCH$_3$ | multiplet |
| 3.80 ppm | —S—CH$_2$—CONH— | singlet |
| 3.40 ppm | cephem CH$_2$ | multiplet |
| 3.00 ppm | HOOC—CH(NH$_2$)—CH$_2$— | doublet |
| 2.00 ppm | —CH$_2$OCOCH$_3$ | singlet |

EXAMPLE 2

7-β-[4-(2′-amino-2′-carboxy)ethylimidazol-2-yl-thioacetamido]-3-[(1-methyl-1H-tetrazol-5-yl)thiomethyl]-3-cephem-4-carboxylic acid was prepared in accordance with the following equation:

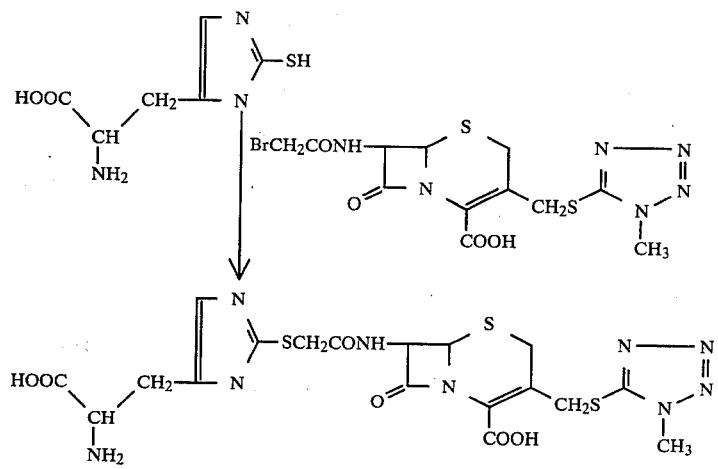

5.6 g of 2-thiol-L-histidine and 10 g of sodium bicarbonate were added to 400 ml of water, and dissolved at 40° C. with heating. After cooling the solution with ice, to the solution was added 13.5 g of 7-β-bromoacetamido-3-[(1-methyl-1H-tetrazol-5-yl)thiomethyl]-3-cephem-4-carboxylic acid. The reaction was carried out with stirring under cooling with ice for 3 hours. The pH of the reaction solution was adjusted to 3.5 with 6N hydrochloric acid to separate precipitates. The precipitates were dried to give 7.3 g of a compound.

The compound was identified as 7-β-[4-(2′-amino-2′-carboxy)ethylimidazol-2-yl-thioacetamido]-3-[(1-methyl-1H-tetrazol-5-yl)thiomethyl]-3-cephem-4-carboxylic acid by the following NMR spectrum of the compound.

| NMR Spectrum (in DMSO-d$_6$): | | |
|---|---|---|
| 9.30 ppm | —CH$_2$CONH— | doublet |
| 6.95 ppm | H-N=/-N (imidazole) | singlet |
| 5.74 ppm | cephem H | multiplet |
| 5.00 ppm | cephem H | doublet |

-continued
NMR Spectrum (in DMSO-d₆):

| 4.30 ppm | (β-lactam-S-CH₂ with COOH, CH₂S—) | multiplet |
| 3.90 ppm | —CH₂S—(N-methyltetrazole) | singlet |
| 3.80 ppm | —SCH₂CONH— | singlet |
| 3.63 ppm | (cephem ring CH₂, S, —N, COOH) | multiplet |
| 2.98 ppm | HOOC—CH(NH₂)—CH₂— | doublet |

EXAMPLE 3

7-β-[4-(2'-amino-2'-carboxy)ethylimidazol-2-yl-thioacetamido]-3-[2-(2-methyl-1,3,4-thiazolyl)thiomethyl]-3-cephem-4-carboxylic acid was prepared in accordance with the following equation:

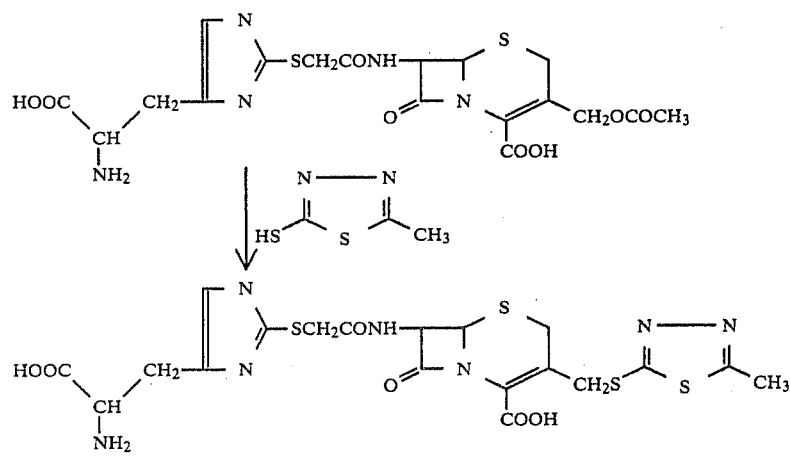

To 100 ml of water were added 5 g of 7-β-[4-(2'-amino-2'-carboxy)ethylimidazol-2-yl-thioacetamido]-3-acetoxymethyl-3-cephem-4-carboxylic acid as obtained in Example 1 and 1.8 g of 2-mercapto-5-methyl-1,3,4-thiadiazole. The reaction was carried out at 60°–70° C. for 4 hours in a nitrogen gas atmosphere while the pH of the reaction mixture was adjusted to 6.0–6.5. After completion of the reaction, the product was subjected to column chromatography packed with XAD-II (product of Rohm and Haas Company) for the purification to give about 4.1 g of a compound.

The compound was identified as 7-β-[4-(2'-amino-2'-carboxy)ethylimidazol-2-yl-thioacetamido]-3-[2-(2-methyl-1,3,4-thiazolyl)thiomethyl]-3-cephem-4-carboxylic acid by the following NMR spectrum of the compound.

NMR Spectrum (in DMSO-d₆):

| 9.43 ppm | —CH₂CONH— | doublet |
| 6.96 ppm | (imidazole H, N, N) | singlet |
| 5.70 ppm | (cephem H, S, CH₂, COOH) | multiplet |
| 5.07 ppm | (cephem H, S, CH₂, COOH) | doublet |
| 4.40 ppm | (cephem S, N, CH₂—S—, COOH) | multiplet |
| 3.80 ppm | —S—CH₂CONH— | singlet |
| 3.72 ppm | | multiplet |
| 3.10 ppm | HOOC—CH(NH₂)—CH₂— | doublet |

-continued

NMR Spectrum (in DMSO-$d_6$):

2.70 ppm 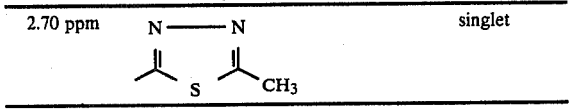 singlet

EXAMPLE 4

7-$\beta$-[4-(2'-amino-2'-carboxy)ethylimidazol-2-yl-thioacetamido]-3-[(1,3,4-triazole)thiomethyl]-3-cephem-4-carboxylic acid was prepared in accordance with the following equation:

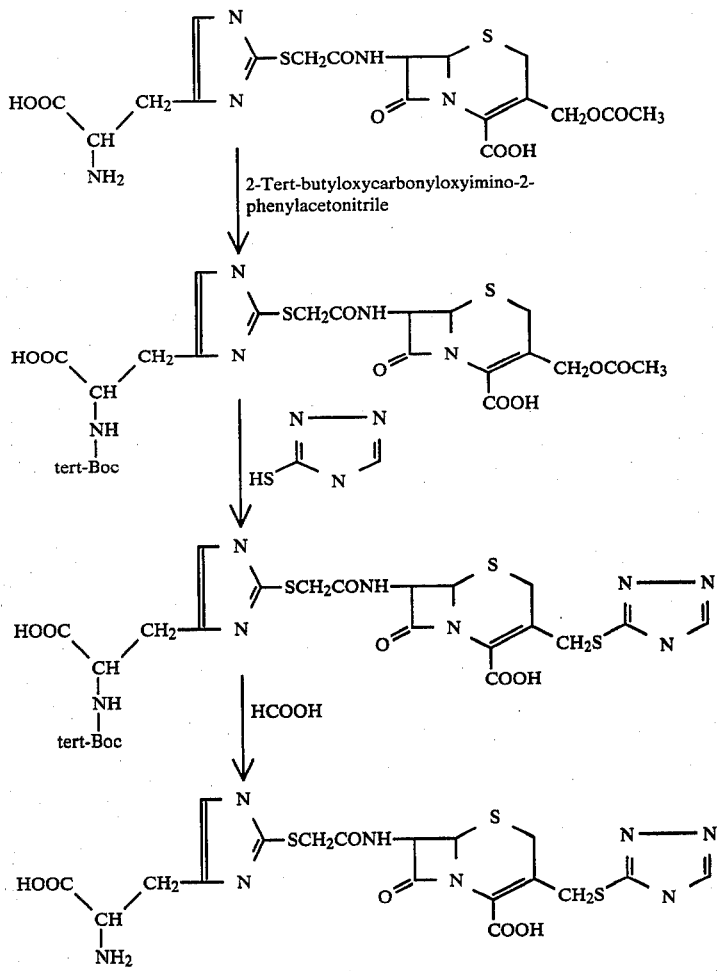

In 60 ml of 50% concentration dioxane and 1 ml of triethylamine was dissolved 4 g of 7-$\beta$-[4-(2'-amino-2'-carboxy)ethylimidazol-2-yl-thioacetamido]-3-acetoxymethyl-3-cephem-4-carboxylic acid as obtained in Example 1. To the solution was added 5 g of 2-tert-butyloxycarbonyloxyimino-2-phenylacetonitrile and the reaction was carried out under cooling with ice for 4 hours.

After completion of the reaction, excess 2-tert-butyloxycarbonyloxyimino-2-phenylacetonitrile was removed by extraction with ethyl acetate. After the pH of the water layer was adjusted to 2, to the water layer was added ethyl acetate as an extraction agent. The ethyl acetate layer was washed with water and dried with anhydrous magnesium sulfate to give 4.8 g of tert-butyloxycarbonylated 7-$\beta$-[4-(2'-amino-2'-carboxy)ethylimidazol-2-yl-thioacetamido]-3-acetoxymethyl-3-cephem-4-carboxylic acid.

To a solution consisting of 100 ml of acetone and 100 ml of water was added 1.8 g of 2-mercapto-1,3,4-triazole. The reaction was carried out by adding 100 ml of acetone solution dissolving 3 g of tert-butyloxycarbonylated 7-$\beta$-[4-(2'-amino-2'-carboxy)ethylimidazol-2-yl-thioacetamido]-3-acetoxymethyl-3-cephem-4-carboxylic acid which had been obtained above to the solution at 50° C. for 4 hours in a nitrogen gas atmosphere while the pH of the reaction solution was adjusted to 6–6.4. After cooling the reaction solution to 5° C., the pH of the solution was adjusted to 2 with 6N hydrochloric acid to give 2.8 g of precipitates. The precipitates were subjected to column chromatography packed with XAD-II (product of Rohm and Haas Company) for the purification to give 2.1 g of a compound. The compound was identified as tert-butyloxycarbonylated 7-$\beta$-[4-(2'-amino-2'-carboxy)ethylimidazol-2-yl-thioacetamido]-3-[(1,3,4-triazole)thiomethyl]-3-cephem-4-carboxylic acid.

In 20 ml of formic acid was dissolved 2.1 g of the tert-butyloxycarbonylated 7-$\beta$-[4-(2'-amino-2'-carboxy)ethylimidazol-2-yl-thioacetamido]-3-[(1,3,4-triazole)thiomethyl]-3-cephem-4-carboxylic acid obtained above, and the reaction was carried out with stirring at 15°–20° C. for one hour. The formic acid was removed under reduced pressure and to the residue thus obtained was added 30 ml of ethyl acetate. The ethyl acetate solution was stirred under cooling with ice to give 1.6 g of a compound.

The compound was identified as 7-β-[4-(2'-amino-2'-carboxy)ethylimidazol-2-yl-thioacetamido]-3-[(1,3,4-triazole)thiomethyl]-3-cephem-4-carboxylic acid by the following NMR spectrum of the compound.

| NMR Spectrum (in DMSO-d$_6$): | | |
|---|---|---|
| 9.40 ppm | —CH$_2$CONH— | doublet |
| 8.07 ppm | 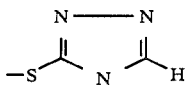 | singlet |
| 6.90 ppm | 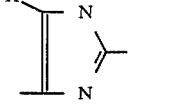 | singlet |
| 5.72 ppm | 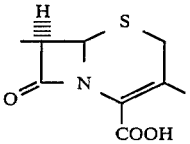 | multiplet |
| 5.03 ppm | | doublet |
| 4.33 ppm | 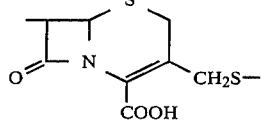 | multiplet |
| 3.83 ppm | —S—CH$_2$CONH— | singlet |
| 3.69 ppm | 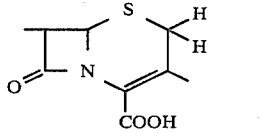 | multiplet |
| 3.05 ppm | HOOC—CH(NH$_2$)—CH$_2$— | doublet |

EXAMPLES 5–7

The same procedures as described in Example 3 were repeated except that the compounds as set forth in Table 1 were employed instead of 5-mercapto-2-methyl-1,3,4-thiadiazole. The products were identified as the compounds having the formulae as set forth in Table 1 by the following NMR spectrum of each product.

| Example No. | Compound | (g) | Product | (g) |
|---|---|---|---|---|
| 5 | 5-Mercapto-1H—1,2,3-triazole | 1.4 | 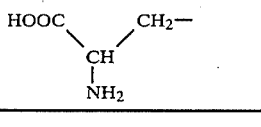 | 3.6 |
| 6 | 5-Mercapto-2-methyl-1,3,4-oxadiazole | 1.6 | 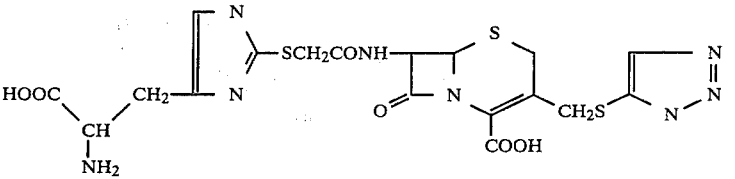 | 3.9 |
| 7 | 5-Mercapto-1-methyl-1H—1,2,3-triazole | 1.6 | 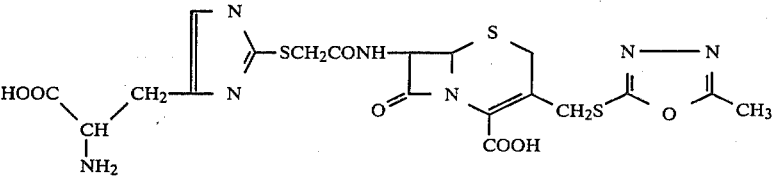 | 3.7 |

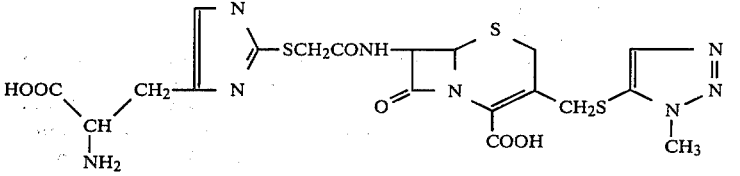

| NMR Spectrum (in DMSO-d$_6$): | | |
|---|---|---|
| Example 5 | | |
| 9.37 ppm | —CH$_2$CONH— | doublet |

-continued
NMR Spectrum (in DMSO-d₆):

| 7.68 ppm | —CH₂S— attached to triazole ring (H, N, N, N) | singlet |
| 6.90 ppm | thiazole-type ring with H | singlet |
| 5.77 ppm | β-lactam-thiazine ring fragment with H, S, COOH | multiplet |
| 4.98 ppm | β-lactam-thiazine ring fragment with H, S, COOH | doublet |
| 4.40 ppm | β-lactam-thiazine ring with CH₂S—, COOH | multiplet |
| 3.82 ppm | —S—CH₂CONH— | singlet |
| 3.65 ppm | β-lactam-thiazine ring with H, H, COOH | multiplet |
| 3.10 ppm | HOOC—CH(NH₂)—CH₂— | doublet |

Example 6
| 9.43 ppm | —CH₂CONH— | doublet |
| 6.88 ppm | thiazole ring with H, N, N | singlet |
| 5.70 ppm | β-lactam-thiazine ring with H, S, COOH | multiplet |
| 5.10 ppm | β-lactam-thiazine ring with H, S, COOH | doublet |

-continued
NMR Spectrum (in DMSO-d₆):

| 4.40 ppm | β-lactam-thiazine ring with CH₂S—, COOH | multiplet |
| 3.80 ppm | —S—CH₂CONH— | singlet |
| 3.70 ppm | β-lactam-thiazine ring with H, H, COOH | multiplet |
| 2.98 ppm | HOOC—CH(NH₂)—CH₂— | doublet |
| 2.57 ppm | N=C(CH₃)—O—C(CH₃)=N | singlet |

Example 7
| 9.40 ppm | —CH₂CONH— | doublet |
| 7.73 ppm | N-methyltriazole ring (H, N, N, N, CH₃) | singlet |
| 6.90 ppm | thiazole ring with H, N, N | singlet |
| 5.74 ppm | β-lactam-thiazine ring with H, S, COOH | multiplet |
| 5.06 ppm | β-lactam-thiazine ring with H, S, COOH | doublet |
| 4.30 ppm | β-lactam-thiazine ring with CH₂S—, COOH | multiplet |
| 3.94 ppm | —S— attached to N-methyltriazole ring | singlet |
| 3.78 ppm | —S—CH₂CONH— | singlet |

-continued

| NMR Spectrum (in DMSO-d₆): | | |
|---|---|---|
| 3.64 ppm | [β-lactam-thiazine structure with S, H, H, COOH] | multiplet |
| 2.96 ppm | HOOC-CH(NH₂)-CH₂- | doublet |

EXAMPLE 8

7-β-[4-(2'-amino-2'-carboxy)ethylimidazol-2-yl-thioacetamido]-3-methyl-3-cephem-4-carboxylic acid was prepared in accordance with the following equation:

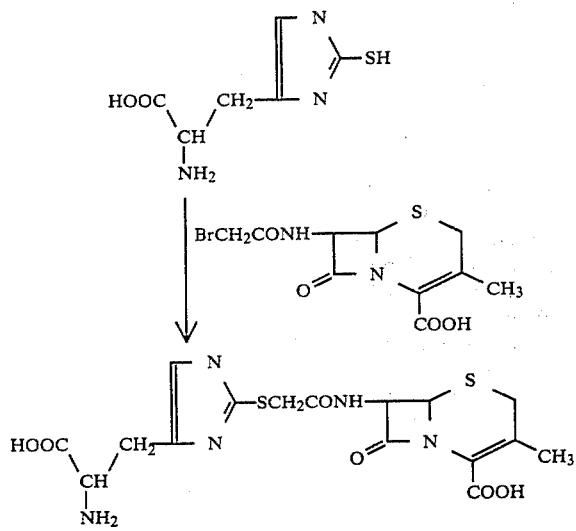

In 300 ml of water and 100 ml of methanol were dissolved 5.6 g of 2-thiol-L-histidine and 10 g of sodium bicarbonate by heating the solution at 30° C. After cooling the solution with ice, to the solution was added 11 g of 7-β-bromoacetamido-3-methyl-3-cephem-4-carboxylic acid and the reaction was carried out for 2 hours. The reaction was further carried out at 20° C. for 4 hours. The pH of the reaction solution was adjusted to 5–6 with 1N hydrochloric acid, and the reaction solution was subjected to column chromatography packed with XAD-II (product of Rohm and Haas Company) for purification to give 8.3 g of a compound.

The compound was identified as 7-β-[4-(2'-amino-2'-carboxy)ethylimidazol-2-yl-thioacetamido]-3-methyl-3-cephem-4-carboxylic acid by the following NMR spectrum of the compound.

| NMR Spectrum (in DMSO-d₆): | | |
|---|---|---|
| 9.42 ppm | —CH₂CONH— | doublet |
| 6.93 ppm | [imidazole H] | singlet |

-continued

| NMR Spectrum (in DMSO-d₆): | | |
|---|---|---|
| 5.62 ppm | [β-lactam H with S, COOH] | multiplet |
| 5.03 ppm | [β-lactam H with S, COOH] | doublet |
| 3.80 ppm | —S—CH₂—CO— | singlet |
| 3.50 ppm | [β-lactam with S, H, H, COOH] | multiplet |
| 3.03 ppm | HOOC-CH(NH₂)-CH₂— | doublet |
| 2.05 ppm | [cephem CH₃, COOH] | singlet |

EXAMPLE 9

7-β-[4-(2'-amino-2'-carboxy)ethylimidazol-2-yl-thioacetamido]-3-methoxy-3-cephem-4-carboxylic acid was prepared in accordance with the following equation:

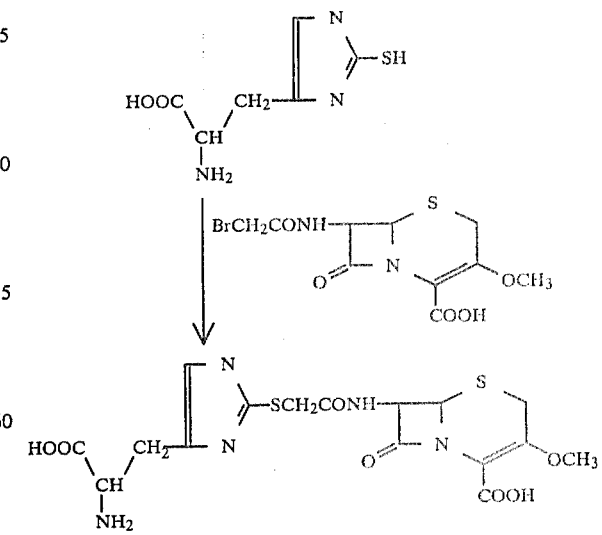

To the solution consisting of 100 ml of water and 150 ml of acetone were added 5.6 g of 2-thiol-L-histidine and 5 g of triethylamine, and further added 10 g of 7-β-bromoacetamido-3-methoxy-3-cephem-4-carboxylic acid at 50° C. The reaction was carried out for 10 hours. After the pH of the reaction solution was adjusted to 5–6 with 1N hydrochloric acid, the acetone was removed under reduced pressure and the solution thus obtained was subjected to column chromatography packed with Amberlite XAD-II (product of Rohm and Haas Company) for the purification to give 7.4 g of a compound.

The compound was identified as 7-β-[4-(2'-amino-2'-carboxy)ethylimidazol-2-yl-thioacetamido]-3-methoxy-3-cephem-4-carboxylic acid by the following NMR spectrum of the compound.

| NMR Spectrum (in DMSO-d₆): | | |
|---|---|---|
| 9.29 ppm | —CH₂CONH— | doublet |
| 6.90 ppm | (imidazole H) | singlet |
| 5.59 ppm | (β-lactam H) | multiplet |
| 5.07 ppm | (β-lactam H) | doublet |
| 3.86 ppm | —OCH₃ | singlet |
| 3.77 ppm | —SCH₂—CO— | singlet |
| 3.60 ppm | (cephem CH₂) | multiplet |
| 3.10 ppm | HOOC-CH(NH₂)-CH₂— | doublet |

EXAMPLE 10

7-β[4-(2'-amino-2'-carboxy)ethylimidazol-2-yl-thioacetamido]-3-chloro-3-cephem-4-carboxylic acid was prepared in accordance with the following equation:

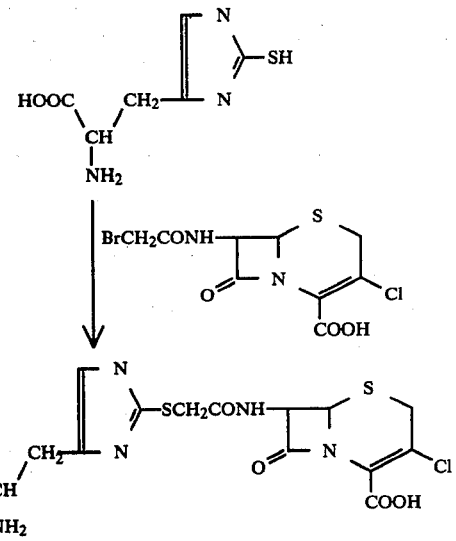

To the solution consisting of 100 ml of water and 100 ml of methanol were added 5.6 g of 2-thiol-L-histidine and 4 g of pyridine, and further added 10 g of 7-β-bromoacetamido-3-chloro-3-cephem-4-carboxylic acid. The reaction was carried out at 5° C. for 6 hours. After removing the methanol from the reaction solution under reduced pressure, the solution thus obtained was subjected to column chromatography packed with XAD-II (product of Rohm and Haas Company) for purification to give 6.9 g of a compound.

The compound was identified as 7-β-[4-(2'-amino-2'-carboxy)ethylimidazol-2-yl-thioacetamido]-3-chloro-3-cephem-4carboxylic acid by the following NMR spectrum of the compound.

| NMR Spectrum (in DMSO-d₆): | | |
|---|---|---|
| 9.37 ppm | —CH₂CONH— | doublet |
| 6.90 ppm | (imidazole H) | singlet |
| 5.72 ppm | (β-lactam H) | multiplet |
| 5.11 ppm | (β-lactam H) | multiplet |
| 3.80 ppm | —SCH₂CO— | singlet |
| 3.70 ppm | (cephem CH₂) | multiplet |

| NMR Spectrum (in DMSO-d6): | | |
|---|---|---|
| 3.08 ppm | HOOC−CH(NH2)−CH2− | doublet |

EXAMPLE 11

7-β-[4-(2'-amino-2'-carboxy)ethylimidazol-2-yl-thioacetamido]-3-cephem-4-carboxylic acid was prepared in accordance with the following equation:

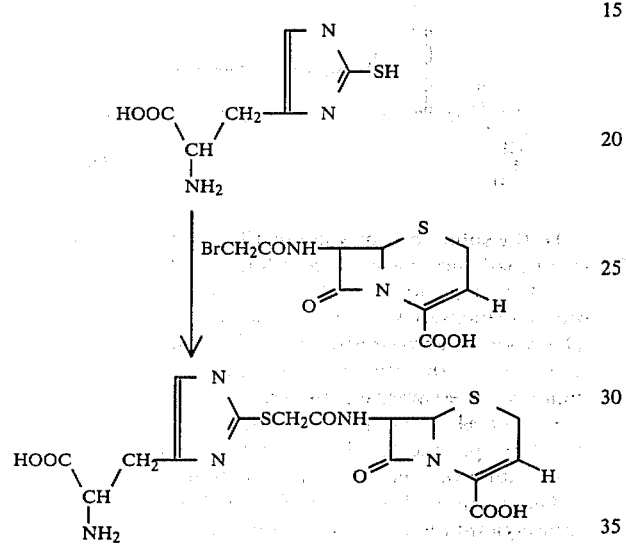

In 200 ml of water were added 5.6 g of 2-thiol-L-histidine and 8 g of sodium bicarbonate, and further added 9 g of 7-β-bromoacetamido-3-cephem-4-carboxylic acid. The reaction was carried out at 5° C. for 15 hours. After completion of the reaction, the reaction solution was subjected to column chromatography packed with XAD-II (product of Rohm and Haas Company) to separate 6.3 g of a compound.

The compound was identified as 7-β-[4-(2'-amino-2'-carboxy)ethylimidazol-2-yl-thioacetamido]-3-cephem-4-carboxylic acid by the following NMR spectrum of the compound.

| NMR Spectrum (in DMSO-d6): | | |
|---|---|---|
| 9.34 ppm | −CH2CONH− | doublet |
| 6.92 ppm | imidazole H | singlet |
| 6.50 ppm | cephem ring with COOH | multiplet |
| 5.82 ppm | cephem ring with H, COOH | multiplet |
| 5.11 ppm | cephem ring with H, COOH | doublet |
| 3.80 ppm | −SCH2CO− | singlet |
| 3.63 ppm | cephem ring with H, H, COOH | multiplet |
| 3.10 ppm | HOOC−CH(NH2)−CH2− | doublet |

EXAMPLE 12

7-β-[4-(2'-amino-2'-carboxy)ethylimidazol-2-yl-thioacetamido]-7α-methoxy-3-acetoxymethyl-3-cephem-4-carboxylic acid was prepared in accordance with the following equation:

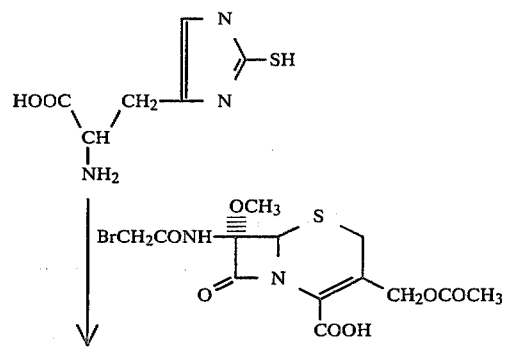

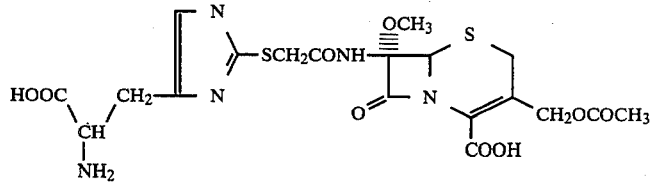

5.6 g of 2-thiol-L-histidine and 10 g of sodium bicarbonate were added to 250 ml of water, and dissolved at 40° C. with heating. After cooling the solution with ice, to the solution was added 12 g of 7-β-bromoacetamido-7α-methoxy-3-acetoxymethyl-3-cephem-4-carboxylic acid and the reaction was carried out at 10° C. for 4 hours. The pH of the product obtained was adjusted to 5-6 with 1N hydrochloric acid, and the product was subjected to column chromatography packed with Amberlite XAD-II (product of Rohm and Haas Company) for the purification to give 10.3 g of a compound.

The compound was identified as 7-β-[4-(2'-amino-2'-carboxy)ethylimidazol-2-yl-thioacetamido]-7α-methoxy-3-acetoxymethyl-3-cephem-4-carboxylic acid by the following NMR spectrum of the compound.

| NMR Spectrum (in DMSO-d$_6$): | | |
|---|---|---|
| 6.93 ppm | 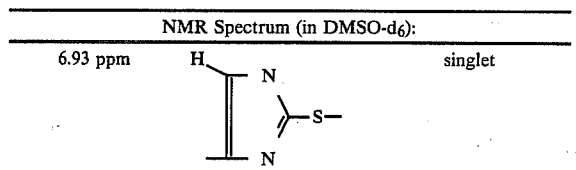 | singlet |
| 5.18 ppm | 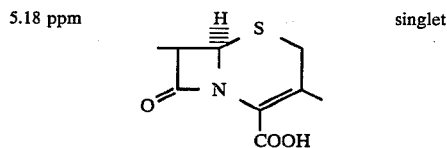 | singlet |
| 4.84 ppm | —CH$_2$OCOCH$_3$ | multiplet |
| 3.76 ppm | —S—CH$_2$CONH— | singlet |

| -continued | | |
|---|---|---|
| NMR Spectrum (in DMSO-d$_6$): | | |
| 3.52 ppm | OCH$_3$ structure | singlet |
| 3.49 ppm | structure with H H | multiplet |
| 2.94 ppm | HOOC—CH(NH$_2$)—CH$_2$— | doublet |
| 2.00 ppm | —CH$_2$OCOCH$_3$ | singlet |

EXAMPLE 13

7-β-[4-(2'-amino-2'-carboxy)ethylimidazol-2-yl-thioacetamido]-7α-methoxy-3-[(1-methyl-1H-tetrazol-5-yl)thiomethyl]-3-cephem-4-carboxylic acid was prepared in accordance with the following equation:

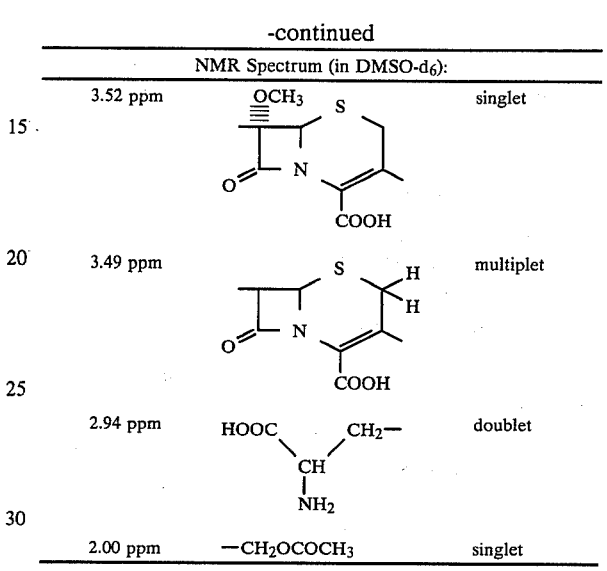

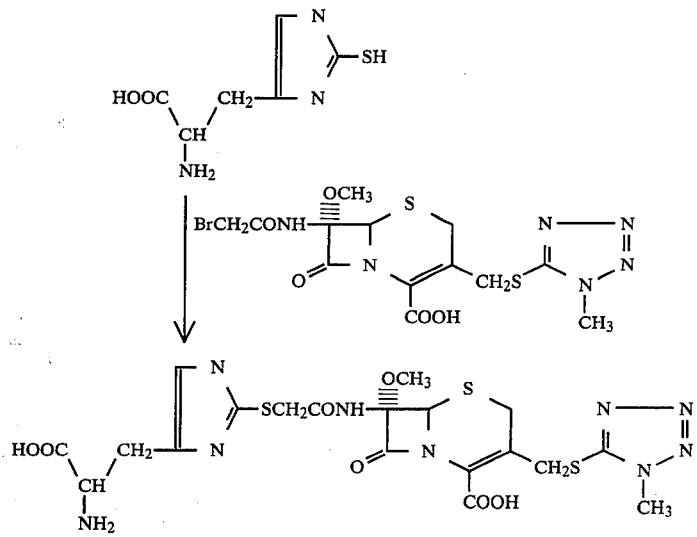

5.6 g of 2-thiol-L-histidine and 10 g of sodium bicarbonate were added to 300 ml of water, and dissolved at 40° C. with heating. After the solution was cooled to 5° C., to the solution was added, 14.0 g of 7-β-bromoacetamido-7α-methoxy-3-[(1-methyl-1H-tetrazol-5-yl)thiomethyl]-3-cephem-4-carboxylic acid and the reaction was carried out with stirring at 5° C. for 3 hours. After completion of the reaction, pH of the reaction solution was adjusted to 3.5 with 6N hydrochloric acid to separate precipitates. The precipitates were dried to give 7.9 g of a compound.

The compound was identified as 7-β-[4-(2'-amino-2'-carboxy)ethylimidazol-2-yl-thioacetamido]-7α-methoxy-3-[(1-methyl-1H-tetrazol-5-yl)thiomethyl]-3-cephem-4-carboxylic acid by the following NMR spectrum of the compound.

| NMR Spectrum (in DMSO-d$_6$): | | |
|---|---|---|
| 6.93 ppm | 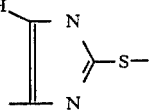 | singlet |
| 5.20 ppm | 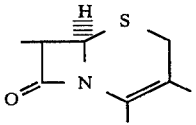 | singlet |
| 4.32 ppm | 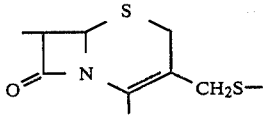 | multiplet |
| 3.92 ppm | 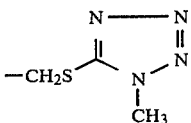 | singlet |
| 3.80 ppm | —SCH$_2$CONH— | singlet |
| 3.59 ppm | 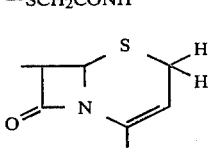 | multiplet |
| 3.49 ppm | 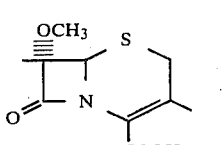 | singlet |
| 2.93 ppm | 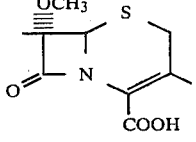 | doublet |

EXAMPLE 14

7-β-[4-(2'-amino-2'-carboxy)ethylimidazol-2-yl-thioacetamido]-7α-methoxy-3-[(1-methyl-1H-tetrazol-5-yl)thiomethyl]-3-cephem-4-carboxylic acid diacetoxymethyl ester was prepared in accordance with the following equation:

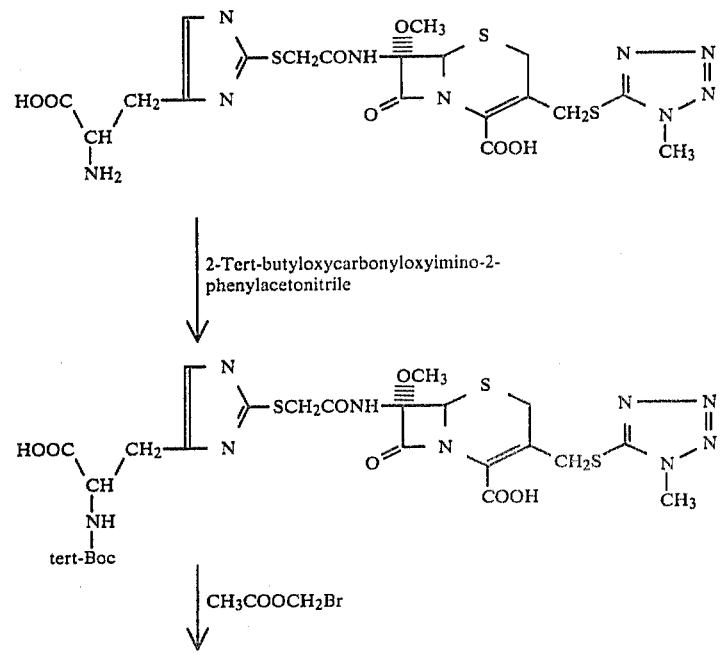

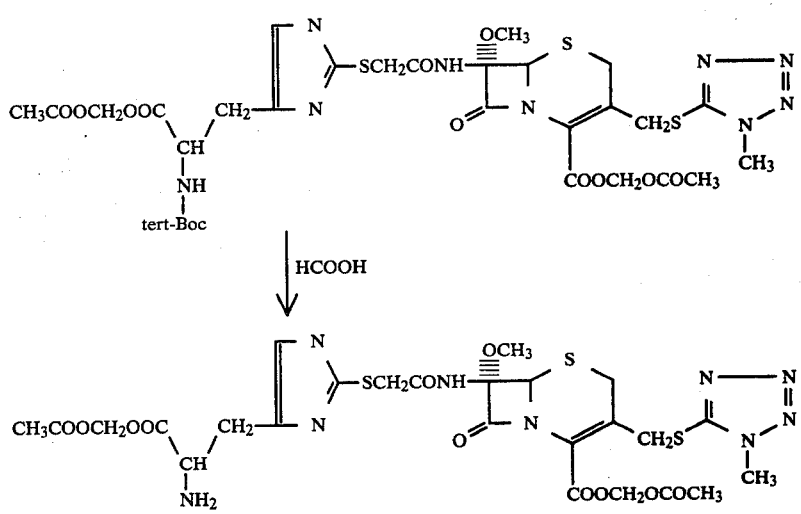

In 60 ml of 50% dioxane and 1.3 ml of triethylamine was dissolved 4 g of 7-β-[4-(2′-amino-2′-carboxy)ethylimidazol-2-yl-thioacetamido]-7α-methoxy-3-[(1-methyl-1H-tetrazol-5-yl)thiomethyl]-3-cephem-4-carboxylic acid as obtained in Example 13. To the solution was added 5 g of 2-tert-butyloxycarbonyloxyimino-2-phenylacetonitrile and the reaction was carried out at 5° C. for 4 hours. After completion of the reaction, excess 2-tert-butyloxycarbonyloxyimino-2-phenylacetonitrile was removed by extraction with ethyl acetate. After the pH of the water layer was adjusted to 2, to the water layer was added ethyl acetate as an extraction agent. Then the ethyl acetate layer was washed with water and dried with anhydrous magnesium sulfate to give 3.8 g of tert-butyloxycarbonylated 7-β-[4-(2′-amino-2′-carboxy)ethylimidazol-2-yl-thioacetamido]-7β-methoxy-3-[(1-methyl-1H-tetrazol-5-yl)thiomethyl]-3-cephem-4-carboxylic acid.

In 50 ml of N,N-dimethylformamide was dissolved 3.8 g of the tert-butyloxycarbonylated 7-β-[4-(2′-amino-2′-carboxy)ethylimidazol-2-yl-thioacetamido]-7α-methoxy-3-[(1-methyl-1H-tetrazol-5-yl)thiomethyl]-3-cephem-4-carboxylic acid obtained and the solution were added 1.5 ml of triethylamine and 1.9 g of bromomethylacetate. The solution was carried out at 5°-10° C. for 10 hours. After removing most N,N-dimethylformamide from the reaction solution, the residue obtained was added with formic acid, and the reaction was carried out at 5° C. for 30 minutes. After completion of the reaction, the formic acid was removed and the residue obtained was subjected to column chromatography packed with Amberlite XAD-II (product of Rohm and Haas Company) for the purification to give 2.3 g of a compound.

The compound was identified as 7-β-[4-(2′-amino-2′-carboxy)ethylimidazol-2-yl-thioacetamido]-7α-methoxy-3-[(1-methyl-1H-tetrazol-5-yl)thiomethyl]-3-cephem-4-carboxylic acid diacetoxymethyl ester by the following NMR spectrum of the compound.

NMR Spectrum (in DMSO-$d_6$):

| ppm | structure | multiplicity |
|---|---|---|
| 6.94 ppm | H on imidazole-S– | singlet |
| 5.22 ppm | β-lactam H | singlet |
| 4.30 ppm | –CH$_2$S– on cephem | multiplet |
| 3.90 ppm | –CH$_2$–S–tetrazole(N-CH$_3$) | singlet |
| 3.80 ppm | –SCH$_2$CONH– | singlet |
| 3.51 ppm | OCH$_3$ on cephem | singlet |
| 2.96 ppm | –OOC–CH(NH$_2$)–CH$_2$– | multiplet |
| 2.00 ppm | –COO–CH$_2$OCOCH$_3$ | singlet |

EXAMPLE 15

7-β-[4-(2′-formamido-2′-carboxy)ethylimidazol-2-yl-thioacetamido]-3-[(1-methyl-1H-tetrazol-5-yl)thiomethyl]-3-cephem-4-carboxylic acid having the following formula was prepared by the following method.

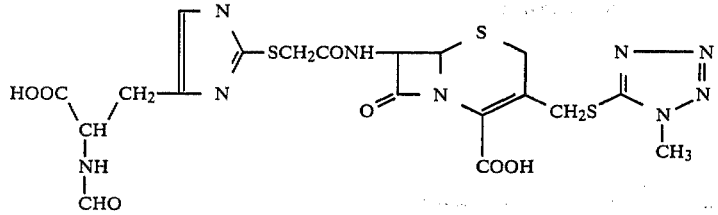

To 50 ml of formic acid was added 5 g of 7-β-[4-(2'-amino-2'-carboxy)ethylimidazol-2-yl-thioacetamido]-3-[(1-methyl-1H-tetrazol-5-yl)thiomethyl]-3-cephem-4-carboxylic acid as obtained in Example 2, and further added 15 ml of acetic anhydride with stirring under cooling with ice for 30 minutes. After continuing the stirring for another 30 minutes, the reaction was carried out at 20° C. for 1 hour. To the reaction mixture was added 100 ml of water and the mixture obtained was concentrated under reduced pressure. To the concentrated mixture was further added 50 ml of water and the concentration was repeated several times to give crystals. The crystals were filtered to give 4.1 g of the desired compound.

| NMR Spectrum (in DMSO-$d_6$): | | |
|---|---|---|
| 9.32 ppm | —CH$_2$CONH— | doublet |
| 8.21 ppm | HOOC-CH(NH-CHO)-CH$_2$— | singlet |
| 6.94 ppm | imidazole H | singlet |
| 5.73 ppm | β-lactam H | multiplet |
| 5.04 ppm | β-lactam H | doublet |
| 4.29 ppm | cephem CH$_2$S | multiplet |
| 3.88 ppm | —CH$_2$S-tetrazole-CH$_3$ | singlet |
| 3.81 ppm | —SCH$_2$CONH— | singlet |
| 3.66 ppm | cephem S-CH$_2$ | multiplet |
| 3.02 ppm | HOOC-CH(NH$_2$)-CH$_2$— | doublet |

EXAMPLE 16

The absorption test of the compounds as obtained in Examples 1–11 were tested by the following method.

Male Wistar rats weighing 180–250 g were fed with only water overnight. The next day the rats were orally administered with 50 mg/kg of a test compound which was dissolved in a buffer solution having pH of 7. The concentration of the compound in blood of the tested animals (one group consisting of 6 animals) was measured 0.5, 1, 2 and 4 hours after the administration by Bioassay method by using Bacillus subtilis ATCC 6633 strain as an indicator bacteria. In the measurement, an ordinary culture medium was employed, and the preparation of the standard solution and other method were carried out in according to Japanese Antibiotical Pharmaceutical Standards. Further, the concentration of the compound in blood was also measured by high performance liquid chromatography. The blood concentration shown below was an average value of each animal group. The results are shown in Table 2.

TABLE 2

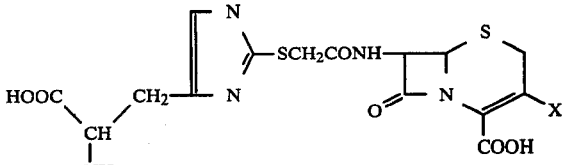

wherein X is shown below

| X | Blood Concentration of the Compound (μg/ml) | | | |
|---|---|---|---|---|
| | 0.5 hr. | 1 hr. | 2 hrs. | 4 hrs. |
| —CH$_2$OCOCH$_3$ | 3.6 | 1.6 | 0.8 | 0.5 |
| 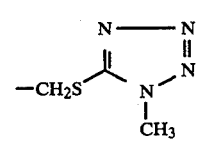 | 4.7 | 2.9 | 2.0 | 1.0 |
| 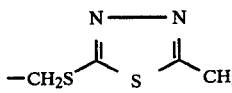 | 11.3 | 12.4 | 13.7 | 9.4 |
| 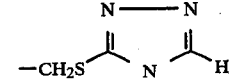 | 2.1 | 1.2 | 0.4 | 0.1 |
| 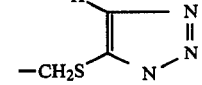 | 12.4 | 13.7 | 14.3 | 10.2 |
| 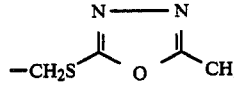 | 8.0 | 5.3 | 3.6 | 1.0 |
| 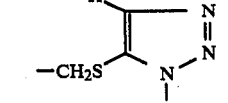 | 4.2 | 2.1 | 0.7 | 0.4 |
| —CH$_3$ | 14.9 | 11.3 | 7.2 | 4.0 |
| —OCH$_3$ | 8.4 | 6.7 | 3.4 | 1.1 |
| —Cl | 7.4 | 5.9 | 3.0 | 1.8 |
| —H | 8.3 | 7.4 | 4.2 | 1.8 |

EXAMPLE 17

The blood concentration of the compounds as obtained in Examples 12-15 and the compounds as obtained in the same manner as in Examples 3 and 12, respectively, was measured. The measurement was carried out in the same manner as Example 16 except that the test compound was suspended in a CMC aqueous solution instead of being dissolved in a buffer solution having pH of 7. The results are shown in Table 3.

TABLE 3

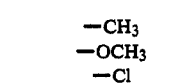

| R$_1$ | R$_2$ and R$_3$ | R$_4$ | X | Blood Concentration of the Compound (μg/ml) | | |
|---|---|---|---|---|---|---|
| | | | | 0.5 hr. | 1 hr. | 4 hrs. |
| H | H | OCH$_3$ | CH$_2$OCOCH$_3$ | 3.9 | 1.7 | 0.4 |

TABLE 3-continued

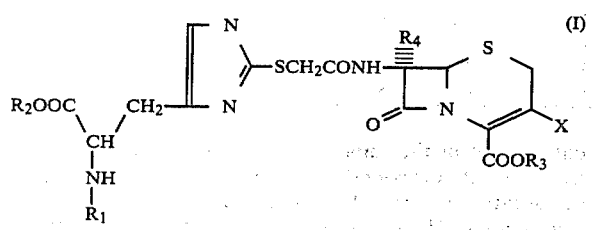

| R₁ | R₂ and R₃ | R₄ | X | Blood Concentration of the Compound (μg/ml) 0.5 hr. | 1 hr. | 4 hrs. |
|---|---|---|---|---|---|---|
| H | H | OCH₃ | CH₂—S—[1-methyl-1H-tetrazol-5-yl] | 4.6 | 3.1 | 1.1 |
| HCO | H | H | CH₂—S—[1-methyl-1H-tetrazol-5-yl] | 3.9 | 2.7 | 1.7 |
| H | CH₂OOCCH₃ | OCH₃ | CH₂—S—[1-methyl-1H-tetrazol-5-yl] | 6.8 | 4.1 | 2.3 |
| CH₃ | H | H | CH₂—S—[2-methyl-1,3,4-thiadiazolyl] | 10.3 | 11.2 | 4.9 |
| H | CH₂OOC—C(CH₃)₃ | OCH₃ | CH₂—S—[1-methyl-1H-tetrazol-5-yl] | 7.2 | 3.9 | 1.6 |

What is claimed is:

1. A cephalosporin compound of the formula (I):

(I)

wherein

X is a hydrogen atom, a chlorine atom, a methyl group, a methoxy group, an acetoxymethyl group or —CH₂SHet wherein Het is a 5-membered heterocyclic ring containing therein 1 to 4 nitrogen, oxygen or sulfur atoms;

R₁, R₂ and R₃ each independently is a hydrogen atom or a protective group which can be pharmaceutically hydrolyzed; and R₄ is a hydrogen atom or a methoxy group;

and the pharmaceutically acceptable salts thereof.

2. The cephalosporin compound of claim 1, wherein —CH₂SHet is (2-methyl-1,3,4-thiazolyl)thiomethyl group, (1-methyl-1H-tetrazol-5-yl)thiomethyl group, (2-methyl-1,3,4-oxadiazole)thiomethyl group, (1H-1,2,3-triazole)thiomethyl group, (1H-1,3,4-triazole)thiomethyl group or (1-methyl-1H-1,2,3-triazole)thiomethyl group.

3. The cephalosporin compound of claim 1, wherein R₁ is a hydrogen atom, a formyl group or a C₁₋₃ alkyl group.

4. The cephalosporin compound of claim 1, wherein R₂ and R₃ each independently is a hydrogen atom, a methoxymethyl group, an acetoxymethyl group, a tert-butylcarboxymethyl group, a 1′-ethoxycarbonyloxyethyl group or a phthalidyl group.

5. The cephalosporin compound of claim 5, wherein R₂ and R₃ each independently is a hydrogen atom, an acetoxymethyl group or a tert-butylcarboxymethyl group.

* * * * *